(12) United States Patent
Hugon et al.

(10) Patent No.: US 9,863,950 B2
(45) Date of Patent: Jan. 9, 2018

(54) METHOD FOR DIAGNOSING NEURODEGENERATIVE DISEASES

(71) Applicant: ASSISTANCE PUBLIQUE—HOPITAUX DE PARIS, Paris (FR)

(72) Inventors: Jacques Hugon, Chantilly (FR); Claire Paquet, Chantilly (FR); Julien Dumurgier, Paris (FR); Francois Mouton-Liger, Villejuif (FR)

(73) Assignee: Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 14/716,201

(22) Filed: May 19, 2015

(65) Prior Publication Data

US 2015/0323535 A1 Nov. 12, 2015

Related U.S. Application Data

(63) Continuation of application No. 13/816,101, filed as application No. PCT/IB2011/053571 on Aug. 10, 2011, now abandoned.

(30) Foreign Application Priority Data

Aug. 11, 2010 (FR) ..................................... 10 03337

(51) Int. Cl.
*G01N 33/53* (2006.01)
*G01N 33/573* (2006.01)
*G01N 33/68* (2006.01)

(52) U.S. Cl.
CPC ....... *G01N 33/573* (2013.01); *G01N 33/6896* (2013.01); *G01N 2333/912* (2013.01); *G01N 2333/91205* (2013.01); *G01N 2800/2821* (2013.01); *G01N 2800/2828* (2013.01); *G01N 2800/2835* (2013.01)

(58) Field of Classification Search
None
See application file for complete search history.

(56) References Cited

PUBLICATIONS

Paccalin et al., Activated mTOR and PKR Kinases in Lymphocytes Correlate with Memory and Cognitive Decline in Alzheimer's Disease, Dementia and Geriatric Cognitive Disorders, 22, pp. 320-326, 2006.
Peel et al., Activation of the Cell Stress Kinase PKR in Alzheimer's Disease and Human Amyloid Precursor Protein Transgenic Mice, Neurobiology of Disease, 14, pp. 52-62, 2003.
Page et al., Activated Double-Stranded RNA-Dependent Protein Kinase and Neuronal Death in Models of Alzheimer's Disease, Neuroscience, 139, pp. 1343-1354, 2006.
Hampel et al., Advances in the Development of Biomarkers for Alzheimer's Disease: From CSF Total Tau and AB1-42 Proteins to Phosphorylated Tau Protein, Brain Research Bulletin, 61, pp. 243-253, 2003.
Mattsson et al., Alzheimer's Disease and CSF Biomarkers: Key Challenges for Broad Clinical Applications, Biomarkers Medicine, 3, pp. 735-737, 2009.
Hugon et al., "Could PKR inhibition modulate human neurodegeneration?" Expert Review of Neurotherapeutics, 9: 1455-157 (2009).
Morel et al., "PKR, the double stranded RNA-dependent protein kinase as a critical target in Alzheimer's disease," Journal of Cellular and Molecular Medicine, 13: 1476-1488 (2009).

*Primary Examiner* — Olga N Chernyshev
(74) *Attorney, Agent, or Firm* — Morgan, Lewis & Bockius LLP

(57) ABSTRACT

The present invention relates to a method for diagnosing, in vitro, a neurodegenerative disease in an individual, in which: the level of the double-stranded RNA-dependent protein kinase (PKR) in a sample of cerebrospinal fluid from the individual is determined; it is deduced therefrom whether the individual is suffering from a neurodegenerative disease.

6 Claims, 6 Drawing Sheets

METHOD FOR DIAGNOSING NEURODEGENERATIVE DISEASES

FIELD OF THE INVENTION

The present invention relates to a method for diagnosing neurodegenerative diseases, particular Alzheimer's disease.

TECHNICAL BACKGROUND

The diagnosis of neurodegenerative diseases is not easy. Thus, for Alzheimer's disease, according to the conventional "NINCDS-ADRDA" criteria (McKhann et al., (1984) *Neurology* 34: 939-944), a distinction is made between possible, probable and definite Alzheimer's disease, with it being possible to establish a diagnosis of definite Alzheimer's disease only post-mortem, after autopsy of the patient and neuropatho-logical examination of the brain demonstrating the existence of, on the one hand, senile plaques and, on the other hand, neurofibrillary degeneration.

The diagnosis of possible or probable Alzheimer's disease is based essentially on clinical criteria and neuropsychological tests which aim firstly to establish whether an individual is exhibiting a dementia syndrome, in general according to the DSM IV criteria (*Diagnostic and Statistical Manual for Mental Disorders*, 4th edition, American Psychiatric Association, 1994), and then to determine the etiology of the dementia. The criteria for dementia essentially comprise the combination of memory impairment and the impairment of other cognitive functions having an impact on socio-professional activities and leading to a decline compared with prior function. The diagnosis is reinforced by monitoring the patient's progress, which makes it possible to specify the causes of the dementia, in particular by ruling out other causes of cognitive decline. In this respect, brain imaging is an important element of the diagnosis through the evaluation of regional hippocampal atrophy, which can however be present in other diseases affecting the elderly, and through the exclusion of other causes of cognitive impairment, such as aftereffects of strokes.

However, it is generally considered that only approximately 85% of cases of probable Alzheimer's disease are confirmed post-mortem. The 15% of false positives generally result from other neurodegenerative diseases, such as frontotemporal dementia, including in particular dementia with Lewy bodies (Delacourte (1998) *Annales de Biologie Cheque* 56: 133-142). The current methodology for diagnosing Alzheimer's disease therefore lacks specificity. In addition, it appears that, between the triggering of the disease, defined by the appearance of the first cognitive impairment, and the first symptoms of dementia that may give rise to the establishing of a diagnosis of possible or probable Alzheimer's disease, there may be a period of more than 10 years (Amieva et al. (2008) *Ann. Neural.* 64: 479-480). The diagnosis of Alzheimer's disease is therefore currently established late, while the disease is at a very advanced stage. The current treatments envisioned for Alzheimer's disease would, however, in order to be effective, need to be carried out right from the beginning of the pathological process, for example while the individual to be treated still exhibits only mild cognitive impairment (MCI), which implies being able to diagnose the disease early.

In fact, supplementary examinations, such as the assaying of biochemical markers in the cerebrospinal fluid of patients, can be carried out in order to improve the diagnosis of Alzheimer's disease. Thus, it has in particular been shown that determining the levels, in the cerebrospinal fluid, of $\beta$-amyloid$_{1-42}$ peptide (A$\beta$42) and the total level of tau (Tubulin Associated Unit) peptide, i.e. both in phosphorylated form and in nonphosphorylated form, makes it possible to diagnose Alzheimer's disease with a sensitivity of 92% and a specificity of 89% (Sunderland at al. (2003) *JAMA* 289: 2094-2103). Since then, a third marker has been added, in addition to A$\beta$42 and total tau (T-tau), namely phosphorylated tau (ptau), in particular phosphorylated on threonine 181 (ptau181). In addition, it has been possible to show that the combination of these three markers makes it possible to detect nascent Alzheimer's disease in individuals suffering from MCI with a sensitivity of 83% and a specificity of 72% (Matteson et al. (2009) *JAMA* 302: 385-393).

However, at the current time, these assays are not carried out routinely, partly because the gain that they enable in terms of reliability and earliness of the diagnosis of Alzheimer's disease is not sufficient to justify having recourse to said assays routinely.

The double-stranded RNA-dependent protein kinase (PKR) is a serine/threonine kinase of which the main target is eukaryotic translation initiation factor 2$\alpha$ (eIF2$\alpha$). PKR exists in a form that is activated by phosphorylation of the threonine at position 446 and/or of the threonine at position 451. It has been possible to demonstrate high levels of activated PKR in particular in the brain of patients suffering from Alzheimer's disease, Huntington's disease and Creutzfeldt-Jakob disease, and also in the blood lymphocytes of patients suffering from Alzheimer's disease (for review see Hugon et al. (2009) *Expert Rev. Neurother.* 9: 1455-1457).

DESCRIPTION OF THE INVENTION

The invention follows from the demonstration, by the present inventors, that determining the level of PKR, in particular in its phosphorylated activated form, in the cerebrospinal fluid of individuals is of use for selectively and specifically diagnosing Alzheimer's disease in these individuals, including at a nascent or early, optionally asymptomatic, stage of the disease.

Thus, the present invention relates to a method for diagnosing, in particular in vitro, a neurodegenerative disease in an individual, wherein:
the level of the double-stranded RNA-dependent protein kinase (PKR) in a biological sample from the individual, in particular a sample of cerebrospinal fluid, is determined,
it is deduced therefrom whether the individual is suffering from a neurodegenerative disease.

The present invention also relates to a method for diagnosing, in particular in vitro, a neurodegenerative disease in an individual, wherein:
the ratio of the level of activated PKR to the total level of PKR in a biological sample from the individual, in particular a sample of cerebrospinal fluid, is determined,
it is deduced therefrom whether the individual is suffering from a neurodegenerative disease.

The present invention also relates to a method for diagnosing, in particular in vitro, a neurodegenerative disease in an individual exhibiting no symptom of dementia, wherein:
the level of the double-stranded RNA-dependent protein kinase (PKR) in a biological sample from the individual, in particular a sample of cerebrospinal fluid, is determined,
it is deduced therefrom whether the individual is suffering from a neurodegenerative disease.

The present invention also relates to a method, in particular in vitro, for determining the risk that an individual exhibiting no symptom of a neurodegenerative disease will suffer from the neurodegenerative disease, wherein:

the level of the double-stranded RNA-dependent protein kinase (PKR) in a biological sample from the individual, in particular a sample of cerebrospinal fluid, is determined, it is deduced therefrom whether the individual is at risk of developing the neurodegenerative disease.

As it is intended here, the expression "neurodegenerative disease" denotes a degenerative disease, i.e. a disease with progressive degradation, affecting the nervous system and in particular the brain.

Preferably, the neurodegenerative disease according to the invention is dementia. Dementia is well known to those skilled in the art; is it generally considered that dementia is characterized by a progressive deterioration of the intellectual function of an individual, thus compromising his abilities to adapt to his environment, in particular in the face of new situations, which results in a loss of his autonomy. Preferably, the symptoms of dementia according to the invention are in particular those defined in the *Diagnostic and Statistical Manual for Mental Disorders,* 4th edition (1994) of the American Psychiatric Association (DSM IV) for dementia of Alzheimer's disease type, namely:

A. The development of multiple cognitive deficits manifesting themselves at the same time through:
  (1) memory impairments (reduced ability to learn new information and to remember previously learnt information);
  (2) one (or more) of the following cognitive impairments:
    (a) aphasia (language impairment),
    (b) apraxia (reduced capacity to carry out motor activities despite intact motor functions),
    (c) agnosia (inability to recognize or identify objects despite intact sensory functions),
    (d) impairment of executive function (i.e. planning, organizing, breaking up into sequences, thinking abstractly).
B. The cognitive deficits of criteria A1 and A2 each cause significant impairments of social or professional function and represent a significant decline compared with a prior level of function.
C. The progression is characterized by a progressive triggering and a continuous cognitive decline.
D. The cognitive deficits of criteria A1 and A2 are not due to any of the following:
  (1) other nervous system diseases causing progressive cognitive and memory deficits (for example, cerebrovascular disease, Parkinson's disease, Huntington's disease, subdural hematoma, normal pressure hydrocephalus, brain tumor);
  (2) systemic diseases known to cause dementia (for example, hypothyroidism, vitamin B12 or folic acid deficiency, niacin deficiency, hypercalcemia, neurosyphilis, HIV infection);
  (3) substance-induced diseases.
E. The deficits do not occur only during a delirium.
F. The trouble cannot be better understood as being caused by another Axis I disorder (within the meaning of DSM IV, i.e. requiring immediate attention) (for example a major depressive disorder, or schizophrenia).

Preferably, the neurodegenerative disease according to the invention is selected from the group consisting of Alzheimer's disease, Huntington's disease, Creutzfeldt-Jakob disease and Parkinson's disease.

Particularly preferably, the neurodegenerative disease according to the invention is Alzheimer's disease.

The individual according to the invention is preferably a human being. The individual according to the invention may exhibit one or more symptoms of dementia or be suffering from dementia.

The individual according to the invention may also not be suffering from dementia or not be exhibiting any symptom of dementia. When not exhibiting dementia, the individual according to the invention may be suffering from cognitive impairment, in particular mild cognitive impairment (MCI), well known to those skilled in the art and in particular defined by Petersen at al., (1999) *Arch. Neurol.* 56: 303-308. An individual is generally defined as having an MCI in the case of subjective complaint associated with an objectively obvious deficit in memory performance with sparing of overall cognitive and intellectual function and integrity of the activities of everyday life. Preferably, an individual with an MCI according to the invention has a score in the Mini Mental State Examination (MMSE) test, in particular in the consensual version of the Groupe de Réflexion sur les Evaulations Cognitives (GRECO) [study group of cognitive evaluations], which is higher than the score corresponding to the 5th percentile, as a function of his age and of his socio-cultural level. Moreover, the individual according to the invention may also not exhibit any cognitive impairment.

When the individual according to the invention is not suffering from dementia, in particular from Alzheimer's disease, or does not exhibit any symptom of dementia, especially of Alzheimer's disease, in particular especially when said individual has an MCI, the methods according to the invention make it possible in particular to determine whether the individual has dementia, in particular Alzheimer's disease, at a nascent or early, even asymptomatic, stage, or whether the individual is at risk of developing dementia, in particular Alzheimer's disease.

Likewise preferably, the level, in a sample of cerebrospinal fluid from the individual, of at least one biological marker of neurodegenerative disease is normal. As it is intended here, the level of a biological marker of neurodegenerative disease is said to be normal when its level is less than the threshold value generally accepted by those skilled in the art for diagnosing the individual as suffering from the neurodegenerative disease with which the marker is associated. Many biological markers of neurodegenerative diseases, in particular of Alzheimer's disease are known to those skilled in the art. Preferably, the biological marker of neurodegenerative disease according to the invention is a biological marker of Alzheimer's disease, in particular chosen from the group consisting of the marker β-amyloid (Aβ), in particular β-amyloid$_{1-42}$ (Aβ42), total tau (T-tau) and phosphorylated tau (ptau), in particular phosphorylated on threonine 181 (ptau181). These markers and the method for measuring their level in a sample of cerebrospinal fluid are well known to those skilled in the art and are in particular defined in Sunderland at al. (2003) *JAMA* 289: 2094-2103, Blennow et al. (2006) Lancet 368: 387-403 and in Mattson et al. (2009) *JAMA* 302: 385-393.

The double-stranded RNA-dependent protein kinase (PKR), also known as E2AK2, is well known to those skilled in the art and is in particular defined in Hugon et al. (2009) *Expert Rev. Neurother.* 9: 1455-1457 or by the accession reference P19525 of the UniProtKB database. As it is intended here, the expression "double-stranded RNA-dependent protein kinase" or "PKR" refers without distinction to nonphosphorylated PKR, to PKR phosphorylated (pPKR) on the threonine at position 446 (pPKR446) and/or on the threonine at position 451 (pPKR451), or to all of these PKR forms. The totality of the phosphorylated and nonphosphorylated forms of PKR in the biological sample of the invention is also known as total PKR.

Thus, in one preferred embodiment of the method of diagnosis or of risk determination of the invention, it is deduced that the individual is suffering from a neurodegenerative disease, in particular from Alzheimer's disease, on the basis of the level of phosphorylated PKR, in particular pPKR446, in the sample, of the level of total PKR in the sample, or of the ratio of the level of phosphorylated PKR, in particular pPKR446, in the sample to the level of total PKR in the sample. In another preferred embodiment of the method of diagnosis or of risk determination of the invention, it is deduced that the individual is suffering from a neurodegenerative disease, in particular from Alzheimer's disease, on the basis of the comparison between:

the level of phosphorylated PKR, in particular pPKR446, in the sample, the level of total PKR in the sample, or the ratio of the level of phosphorylated PKR, in particular pPKR446, in the sample to the level of total PKR in the sample, and at least one predefined value, in particular when the level of phosphorylated PKR, in particular pPKR446, in the sample, the level of total PKR in the sample, or the ratio of the level of phosphorylated PKR, in particular pPKR446, in the sample to the level of total PKR in the sample is greater than the predefined value.

The predefined value according to the invention can be readily determined by those skilled in the art. It may in particular be the average level of PKR according to the invention, or a multiple greater than 1 of this average level, in samples of CSF from control individuals not suffering from cognitive impairment. It may also be a threshold value obtained from Receiving Operating Characteristics (ROC) curves established for total PKR, phosphorylated PKR, in particular pPKR446, or the ratio of the level of phosphorylated PKR, in particular pPKR446, in the sample to the level of total PKR in the sample, by fixing particular selectivity and specificity values, in particular for maximizing the sum of the selectivity and of the specificity, as is illustrated in the examples which follow. Thus, by way of example, according to the invention, an individual will be diagnosed as having Alzheimer's disease when the ratio of the level of phosphorylated PKR, in particular pPKR446, in the sample to the level of total PKR in the sample is greater than 0.76 or 0.77.

Moreover, in another particular embodiment, the method of diagnosis or of risk determination according to the invention also comprises the determination of the level of at least one other biological marker of neurodegenerative disease, in particular of Alzheimer's disease, as defined above.

The biological sample according to the invention is preferably a fluid biological sample, more preferably of cerebrospinal fluid (CSF). Those skilled in the art are well aware how to obtain CSF from an individual, for example by lumbar puncture.

Preferably, in the method according to the invention, the level of PKR according to the invention in the biological sample according to the invention is determined by means of an immunological method, i.e. a method using antibodies, in particular monoclonal antibodies, antibody fragments comprising the part of the antibody which binds specifically to the antigen, or else aptamers, specifically directed against PKR, i.e. which essentially do not bind to any other constituent of the biological sample, in particular of the sample of CSF. As will emerge clearly to those skilled in the art, antibodies that are used for measuring the level of total PKR are directed against a part of PKR that is not modified by phosphorylation; conversely antibodies that are used for measuring the level of pPKR446 or pPKR451 bind to the phosphorylated part of PKR (and not to the same part when it is not phosphorylated). Such anti-PKR antibodies are well known to those skilled in the art. The immunological methods according to the invention are well known to those skilled in the art and cover in particular Western blotting or the ELISA technique.

The invention will be further illustrated in a non-limiting manner by means of the figures and examples which follow.

DESCRIPTION OF THE FIGURES

FIGS. 1 to 3 give box plot representations of the levels (arbitrary units), measured in the CSF of patients suffering from Alzheimer's disease (AD), of total PKR (PKR) (FIG. 1), of pPKR446 (pPKR) (FIG. 2) and of the pPKR446/total PKR ratio multiplied by 100 (pPKR/PKR) (FIG. 3), compared with those measured in the CSF of control individuals not suffering from cognitive impairment (control).

FIGS. 4 to 6 represent the ROC curves giving the selectivity (y-axis) and 1-specificity (y-axis) of the diagnosis of Alzheimer's disease on the basis of the level of total PKR (FIG. 4), of pPKR446 (FIG. 5) and of the pPKR446/total PKR ratio (FIG. 6).

FIG. 7 represents the relationship between the pPKR446/total PKR ratio multiplied by 100 (pPKR/PKR, y-axis, arbitrary units) and the level of ptau181 (ptau, x-axis, pg/ml) in the CSF and also the corresponding linear correlation line.

FIG. 8 represents the ratio of the level of pPKR446 to the level of total PKR (y-axis, arbitrary units) in the CSF of patients suffering from Alzheimer's disease (AD), in particular with normal (AD-PLn) or intermediate (AD-PLi) levels of the Aβ42, T-tau and ptau181 markers; of control individuals without cognitive impairment (HC); of controls with cognitive impairment unrelated to Alzheimer's disease (CC); of individuals with alcohol dementia (OH); and of individuals with mild cognitive impairment (MCI).

FIGS. 9 to 11 represent, respectively, the levels in the CSF of total PKR and of pPKR446 (in optical density units), and also the pPKR446/total PKR ratio (no unit), measured in example 3, for control individuals (NC), individuals suffering from amnestic mild cognitive impairment (MCI) and individuals suffering from Alzheimer's disease. The solid horizontal bars represent the mean values and the dashed horizontal bars the threshold value.

EXAMPLES

Example 1

1. Patients and Methods

Figure 1:
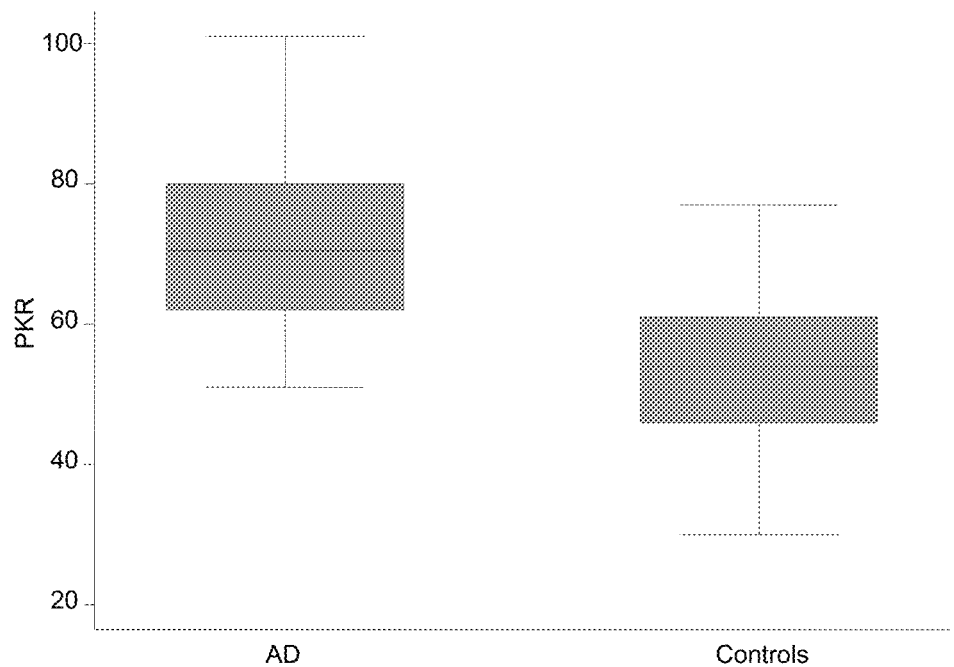
FIGS. 1, 2 and 3

Patients 46 patients diagnosed as having Alzheimer's disease (AD) and 39 control individuals not having Alzheimer's disease were included in the study. The AD patients were included on the basis of the NINCDS-ADRDA criteria. All the patients originated from the Centre Mémoire [Memory Center] of the Lariboisière hospital (Paris, France). None of the control individuals exhibited any cognitive impairment and met the criteria for Alzheimer's disease. Samples of cerebrospinal fluid (CSF) were collected after lumbar puncture in the context of the conventional diagnostic procedure, in combination with a neurological examination, routine blood tests, neuropsychological tests and MRI imaging of the brain. The study was approved by the ethics committee of the Paris Nord Bichat hospital.

Analysis of the CSF by Western Blotting: Determination of the Levels of Total PKR and PKR Phosphorylated on Threonine 446 (pPKR446)

The samples of CSF were pretreated with a column (ProteoExtract™, Calbiochem®) in order to remove albumin and the IgGs, and then prepared, according to standard techniques, for Western blotting. The protein concentrations were determined using the Micro BCA Protein Assay kit (Thermo Scientific) according to the manufacturer's instructions. The samples of CSF were separated on a NuPAGE BisTris 4-12% polyacrylamide gel (Invitrogen) and then electrotransferred onto nitrocellulose membranes (GE Healthcare). The membranes were incubated with rabbit primary antibodies recognizing, respectively, pPKR446 specifically at phosphorylated threonine 446 and all of the PKR proteins (SantaCruz), blocked in 5% milk in PBS, and then incubated in the presence of the IR Dye™ 800 fluorophore coupled to an anti-rabbit antibody (Rockland Immunochemical Inc.) diluted to 1/5000. The bound proteins were visualized by means of the Odyssey imaging system (LI-COR Biosciences) and then quantified by densitometry using the Multigauge software (Fuji). The pPKR446/total PKR ratio was determined for each patient and each control individual. All the results were adjusted relative to an internal control (human brain suffering from Alzheimer's disease). The statistical analysis of the quantification was carried out by means of version 5 of the Prism software (GraphPad).

Analysis of the CSF by ELISA: β-Amyloid$_{1-42}$ (Aβ42), Total Tau (T-Tau), Tau Phosphorylated on Threonine 181 (ptau181)

The levels of Aβ42, T-tau and ptau181 were determined by ELISA (Innotest tests Abeta, Innotests tau, Innotests p181tau, Innogenetics, Ghent, Belgium) in the same samples of CSF as those used for determining the levels of total PKR and of pPKR446 according to the manufacturer's recommendations.

Statistical Analysis

Descriptive statistics were used to describe the characteristics of the patients and of the controls. The groups were compared using the Student's t-test for the continuous measurements and the chi$^2$ test for the proportions. The distributions of the levels of total PKR and of ppKR446, and also the ratio of the level of pPKR446 to the level of total PKR (pPKR446/total PKR) within the two groups (patients and controls) were represented by the box plot graph method. ROC (Receiving Operating Characteristics) curve analysis was used to determine the best cutoff values for the level of the CSF markers measured and to calculate the area under the curves (AUC). The best cutoff values were defined as giving the highest sum of the sensitivity and of the specificity. The Spearman correlation coefficient between, on the one hand, PKR and pPKR446 and, on the other hand, Aβ42, T-tau and ptau was also determined.

2. Results

The characteristics of the individuals studied are given in table 1 below:

TABLE 1

Characteristics of the individuals in the study

|  | Controls (N = 39) | Alzheimer's (AD) (N = 46) | P |
|---|---|---|---|
| Age, in years | 69.5 (10.8) | 70.7 (8.9) | 0.59 |
| Number of women (%) | 21 (62) | 26 (57) | 0.64 |
| MMSE | 27.1 (2.9) | 19.4 (6.4) | <0.001 |
| Aβ42 in pg/ml | 798.7 (121.6) | 409.8 (149.1) | <0.001 |
| T-tau, in pg/ml | 189.2 (55.1) | 598.0 (328.0) | <0.001 |
| ptau, in pg/ml | 42.5 (11.4) | 107.6 (51.9) | <0.001 |
| Total PKR, arbitrary units | 53.7 (10.6) | 71.9 (12.2) | <0.001 |
| pPKR446, arbitrary units | 30.9 (19.5) | 94.9 (38.5) | <0.001 |
| pPKR446/PKR ratio | 0.59 (2.47) | 1.28 (3.71) | <0.001 |

Except for the number of women, the values indicated represent the mean of the individuals, the standard deviation is indicated between parentheses.
MMSE: score in the Mini Mental Status Examination cognitive test.

The data in the table indicate that the mean values of the PKR and activated PKR (pPKR446) concentrations and of the pPKR446/PKR concentration ratio are significantly higher in the CSF of the patients suffering from Alzheimer's disease compared with the control individuals.

Figure 2:
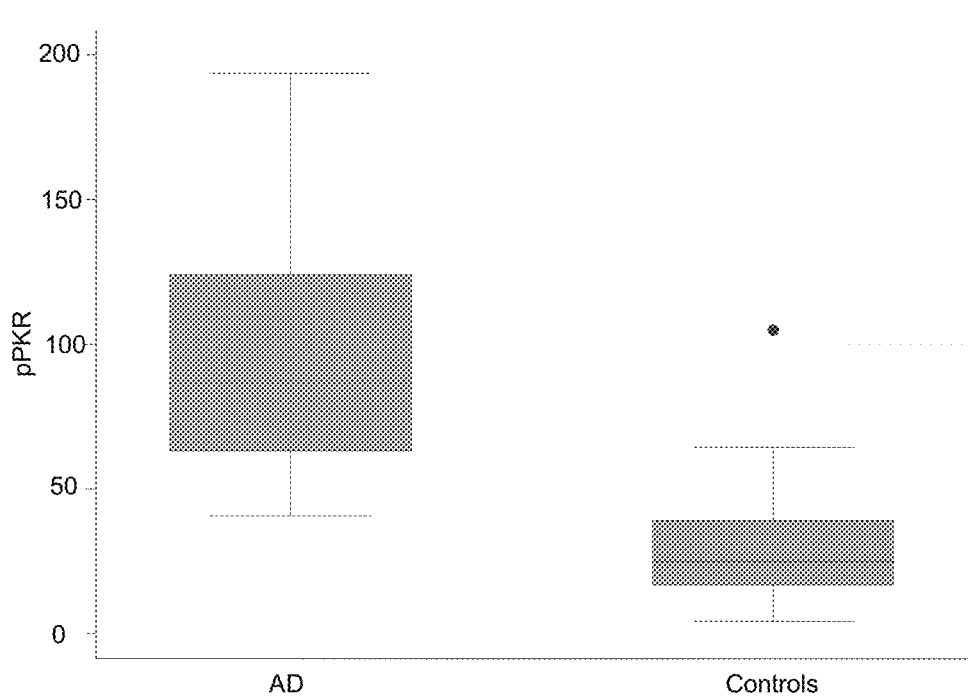
Figure 3:
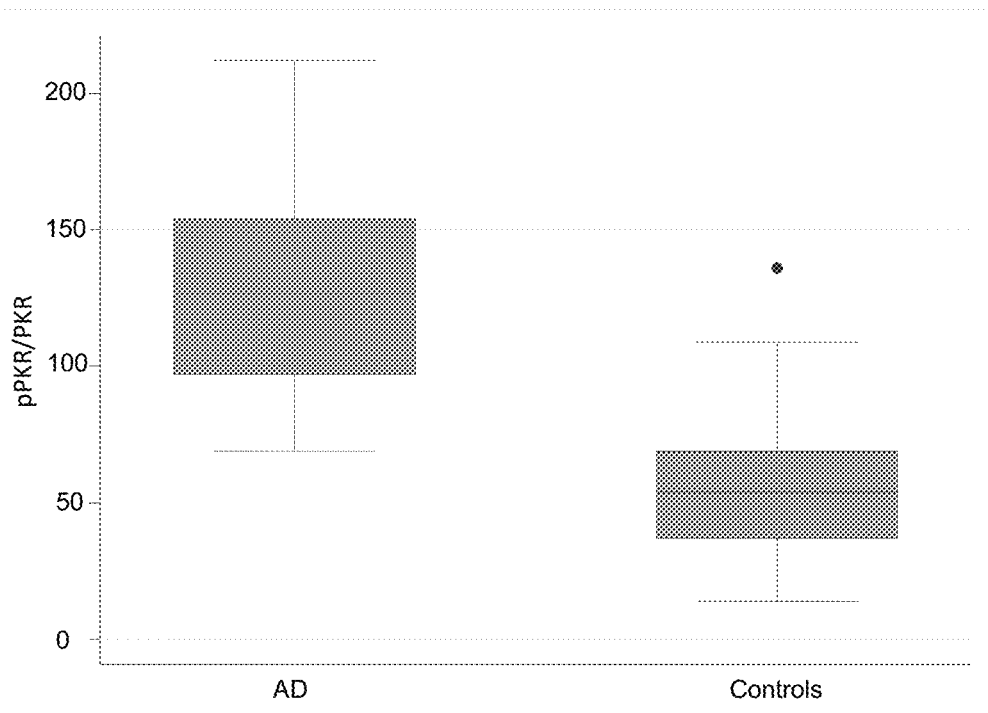
Figure 4:
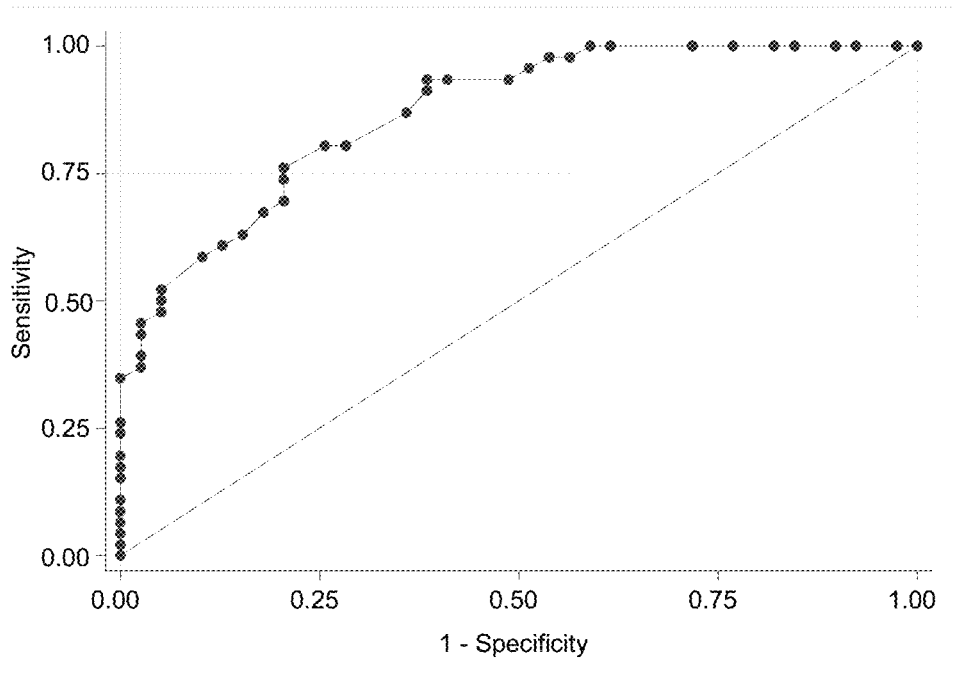
FIGS. 4, 5 and 6
Figure 5:
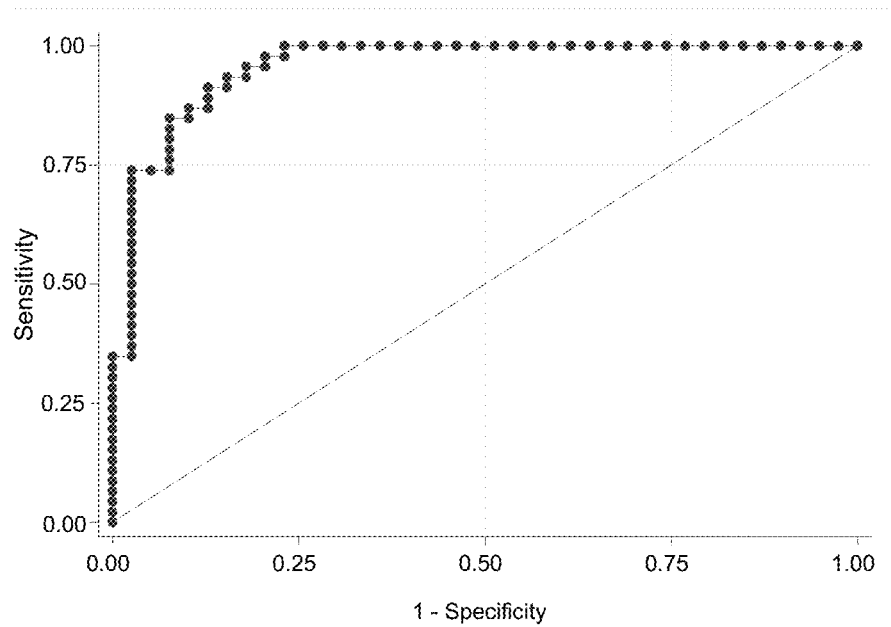
Figure 6:
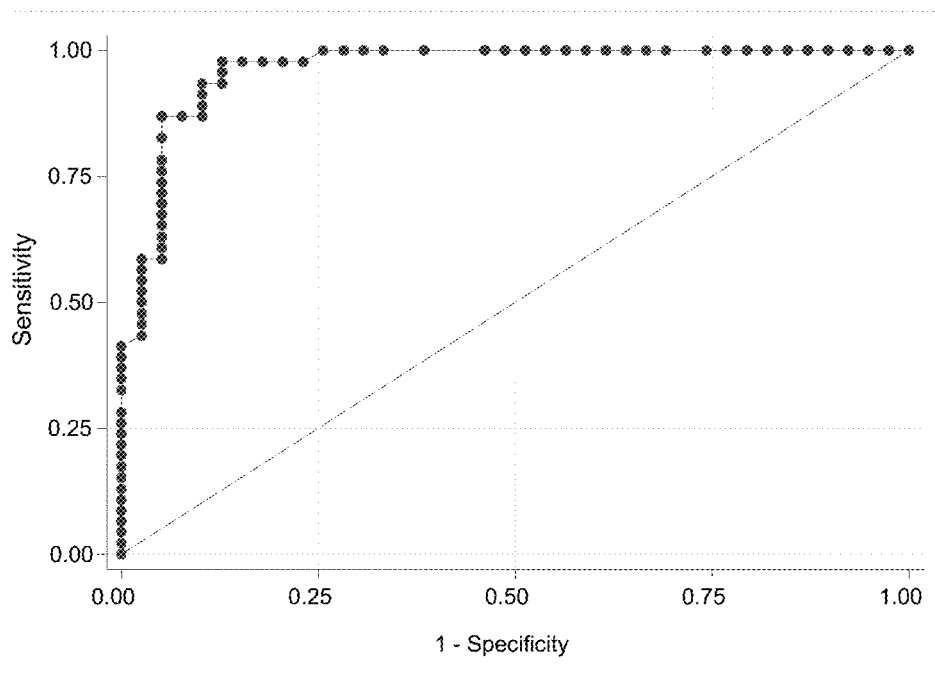

These observations are confirmed for the data as a whole by the box plot representations given in FIGS. 1, 2 and 3. In particular, the set of values obtained for the pPKR446 concentrations and for the pPKR446/total PKR ratio of the control individuals is significantly lower than that of the patients suffering from Alzheimer's disease.

Moreover, the ROC curves were established for total PKR, pPKR446 and the pPKR446/total PKR ratio. The sensitivity and specificity data taken from these curves are given in table 2 below:

TABLE 2

Area under the curve (AUC) of the ROC curves

| Biomarkers | AUC | Threshold | Sensitivity | Specificity | Correctly screened |
|---|---|---|---|---|---|
| Total PKR | 0.87 | 62 | 76.1 | 79.5 | 77.7 |
| pPKR446 | 0.96 | 40 | 100 | 76.9 | 89.4 |
| pPKR446/total PKR | 0.96 | 77 | 97.8 | 87.2 | 92.9 |
| Aβ42 | 0.95 | 584 | 94.4 | 90.9 | 91.9 |
| T-tau | 0.97 | 282 | 93.2 | 100 | 95.2 |
| ptau181 | 0.98 | 61 | 90.9 | 100 | 93.6 |

The use of the levels of total PKR and especially of activated PKR (pPKR446) and of the pPKR446/total PKR ratio makes it possible to detect patients suffering from Alzheimer's disease. It is in particular observed that determining the level of activated PKR (pPKR446) and the pPKR446/total PKR ratio enables a more sensitive detection of Alzheimer's disease than that offered by the diagnostic markers Aβ42, T-tau and ptau181.

Figure 7:
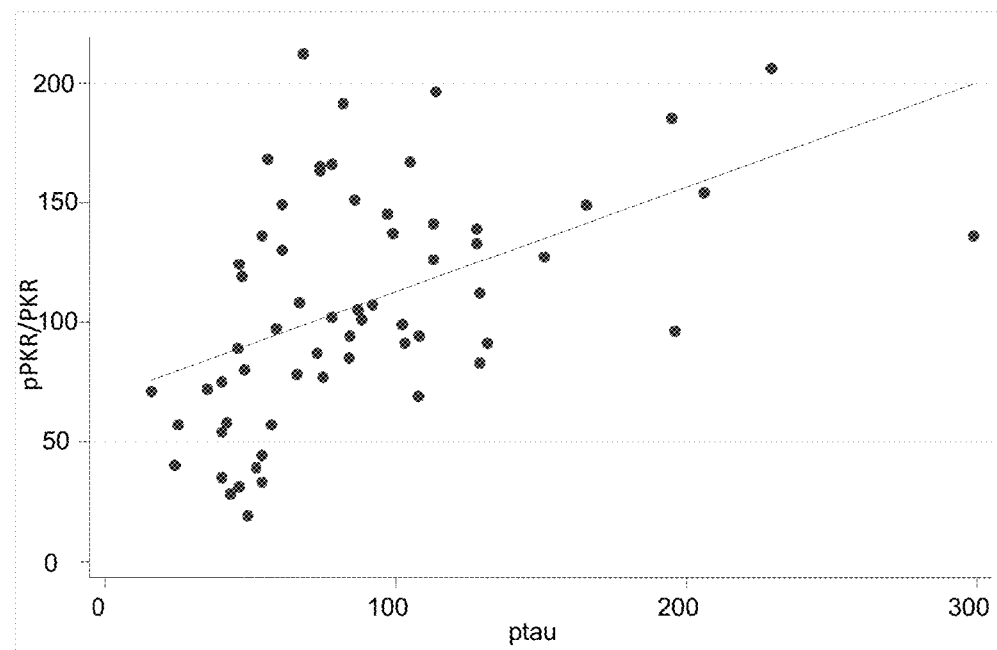
FIG. 7

The Spearman correlation coefficients between, on the one hand, the Aβ42, T-tau and ptau181 markers and, on the other hand, the total PKR, pPKR446 and pPKR446/total PKR markers are given in table 3 below and in FIG. 7.

TABLE 3

Spearman correlation coefficients

|  | Aβ42 | | T-tau | | ptau181 | |
|---|---|---|---|---|---|---|
|  | Rho | P | Rho | P | Rho | P |
| Total PKR | −0.37 | 0.003 | 0.45 | <0.001 | 0.46 | <0.001 |
| pPKR446 | −0.47 | <0.001 | 0.56 | <0.001 | 0.58 | <0.001 |
| pPKR446/total PKR | −0.47 | <0.001 | 0.56 | <0.001 | 0.57 | <0.001 |

The Spearman correlation coefficients between, on the one hand, the Aβ42, T-tau and ptau181 markers and, on the other hand, the total PKR, pPKR446 and pPKR446/PKR markers are relatively low. These two groups of markers therefore appear to be relatively independent of one another, which leads one to envision that combining the markers of the invention with Aβ42, T-tau and ptau181 could improve the diagnostic efficiency of the latter.

Example 2

Figure 8:
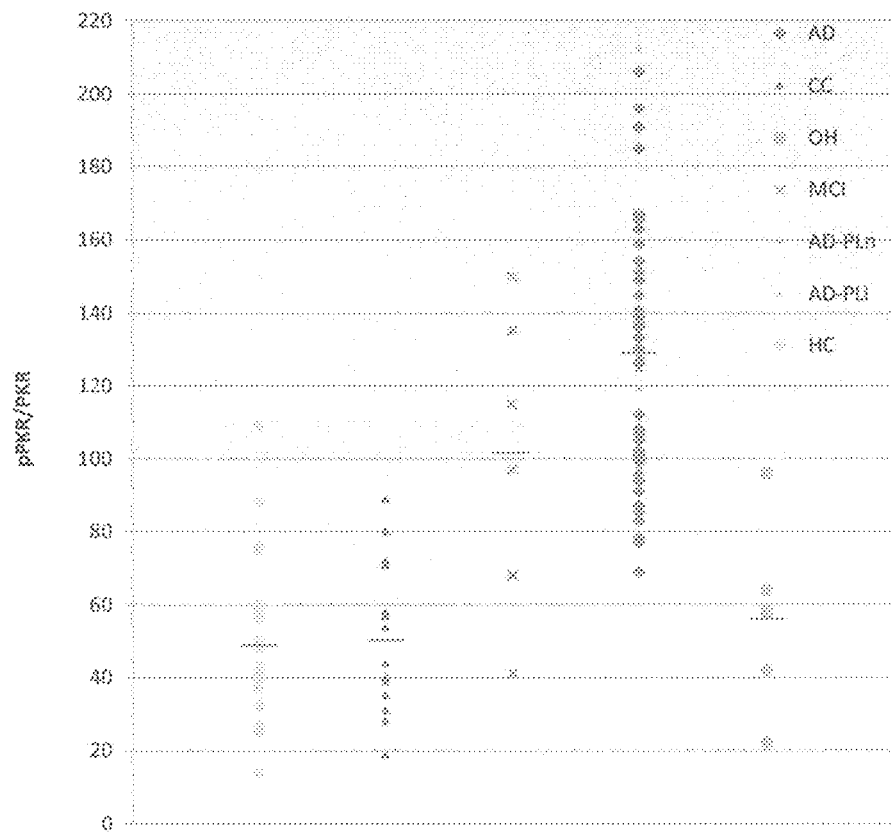
FIG. 8

By following the methodology of example 1, the inventors also compared the ratio of the level of pPKR446 to the level of total PKR in the CSF of patients suffering from Alzheimer's disease (AD), selected as is indicated in example 1, with the same ratio measured in the CSF of control individuals without cognitive impairment (HC), of controls with cognitive impairment unrelated to Alzheimer's disease (for example, secondary to depression or to another psychiatric disorder, to frontotemporal dementia, to vascular dementia or to a Lewy body disease) (CC), of individuals with alcohol dementia (OH) and of individuals with mild cognitive impairment (MCI) (FIG. 8).

It is observed that the mean value of the pPKR446/total PKR ratio is higher in the CSF of patients suffering from Alzheimer's disease than in the CSF of control individuals without cognitive impairment (as was already seen in example 1) and also in the CSF of individuals with alcohol dementia, of which the mean value of the ratio is moreover similar to that of the controls without cognitive impairment. In the present case, this indicates that the elevation of the pPKR446/total PKR ratio is specific for Alzheimer's disease and possibly more generally for neurodegenerative dementia.

It is also observed that the mean value of the pPKR446/total PKR ratio in the CSF of individuals suffering from mild cognitive impairment (MCI) is intermediate compared with that of the patients suffering from Alzheimer's disease and with that of the control individuals without cognitive impairment. Insofar as the annual rate of conversion of individuals with MCI into individuals suffering from Alzheimer's disease is approximately 15%, some of the individuals not subsequently developing Alzheimer's disease, it is probable that the elevation of the pPKR446/total PKR ratio in individuals suffering from MCI is an indication of the presence of nascent or early-stage Alzheimer's disease (i.e. before the appearance of dementia symptoms) or that it is an indication of individuals at risk of developing Alzheimer's disease in the short term. Moreover, the mean value of the pPKR446/total PKR ratio in the CSF of control individuals with cognitive impairment unrelated to Alzheimer's disease is similar to that of the controls without cognitive impairment, which indicates that the elevation of the pPKR446/total PKR ratio in individuals suffering from MCI is specific for Alzheimer's disease and possibly more generally for neurodegenerative disorders.

Finally, it is observed that, although some of the patients suffering from Alzheimer's disease exhibit levels of the Aβ42, T-tau and ptau181 markers in the CSF that are normal (AD-PLn) or intermediate i.e. between the normal limit and the pathological limit (AD-PLi), the value of the pPKR446/total PKR ratio is elevated, which indicates that this ratio may be of use for identifying patients suffering from Alzheimer's disease who could not be identified using conventional markers.

Example 3

A clinical study, complementary to that of example 1, was carried out.

1. Patients and Methods

Patients

For one year, 119 consecutive individuals visiting the Centre Mémoire [Memory Center] of the Lariboisière hospital (Paris, France) for a cerebrospinal fluid (CSF) analysis in order to study cognitive impairment were included in the study. Excluded from the study, owing to their low number, were 5 individuals with frontotemporal dementia or a Lewy body disease and 6 individuals having had a stroke, having a score greater than 4 on the Hachinksi ischemic scale or having a cardiovascular disease with a visible consequence in brain MRI (multiple large vessel infarctions, strategically placed single infarction, multiple basal ganglion, gaps in the white matter, extensive periventricular lesions of the white matter). Before the diagnosis, all the individuals were subjected to a standardized clinical examination including a medical history and physical and neurological examinations. Laboratory tests were carried out for all the individuals, including a measurement of serum cobalamin and folate levels, a chemistry panel, thyroid function tests, syphilis serology, a measurement of reactive protein C levels, a complete blood workup, and a brain MRI. The diagnoses were established by a multidisciplinary team of neurologists and neuropsychologists specializing in cognitive impairment. The Alzheimer's disease diagnosis was established in accordance with the NINCDS-ADRDA criteria (McKhann et al. (1984) *Neurology* 34: 939-44) and the individuals suffering from amnestic mild cognitive impairment (MCI) met the usual criteria (Petersen et al. (2001) *Arch. Neurol* 58: 1985-92). This study was approved by the ethics committee of the University Hospital Centers of Paris (CEERB CHU Bichat, Paris, France). All the individuals and carers gave their informed written consent regarding the analysis of the CSF.

Procedures Relating to CSF

The lumbar punctures were performed on the individuals after a period with no food within a month following the clinical diagnosis. The CSF was connected in a 12 ml polypropylene tube. Within two hours, the samples of CSF were centrifuged at 1800 g for 10 min at 4° C. A small amount of CSF was used for the routine analyses, including a total cell count, a bacteriological test and the total glucose and protein levels. The CSF was divided up into 500 µl polypropylene tubes and stored at −80° C. while awaiting analysis. The levels of Aβ42, T-tau and ptau181 in the CSF were measured using the Innotest ELISA sandwich test according to the manufacturer's instructions (Innogenetics, Ghent, Belgium). The biomarker positivity criteria were defined as a function of the abnormalities of the levels of Aβ42, T-tau and ptau181, according to the cutoff thresholds used at the Centre Mémoire [Memory Center] of the Lariboisière hospital (Aβ42<500 pg/ml; T-tau>302 pg/ml; ptau181>65 pg/ml). The set of biological analyses was carried out in a single laboratory. The team of biologists involved in the analysis of the CSF was not informed of the clinical diagnosis. The quality of the CSF analysis was validated by a European consortium (quality control program for CSF biomarkers of the Alzheimer's association).

Determination of the Levels of Total PKR and of pPKR446 in the CSF

The samples of CSF were pretreated on a column (ProteoExtract™, Calbiochem®, Darmstadt, Germany) in order to remove albumin and the IgGs, according to the manufacturer's instructions. Briefly, 800 µl of equilibration buffer were added to the column in order to rehydrate it. 300 µl of each sample of CSF were then deposited on individual disposable columns and eluted by gravity. The filtered samples were obtained after elution of the column by means of two washes with a specific binding buffer provided by the manufacturer. The samples having had the IgG and albumin removed were aliquoted and stored at −20° C. The efficiency of the filtration step was evaluated by means of an immunolabeling analysis using an antibody directed against human serum albumin (Santa Cruz, Danvers, Mass., United States). The protein concentrations were determined using the Micro BCA Protein Assay kit (Thermo Scientific, Cergy-Pontoise, France) according to the manufacturer's instructions.

The CSF protein samples were separated on a NuPAGE BisTris 4-12% polyacrylamide gel (Invitrogen) and then electrotransferred onto nitrocellulose membranes (GE Healthcare, Chalfont St. Giles, United Kingdom) at 400 mA per gel in 25 mM Tris (pH 8.3), 200 mM glycine and 20% ethanol. After the transfer, the nitrocellulose membranes were blocked in 5% (weight/volume) of milk in TBS, and then incubated with the primary antibody.

The following primary antibodies were used. A rabbit anti-PKR446 antibody (Santa Cruz), a rabbit anti-PKR antibody (Cell Signaling, Beverly, Mass., United States), a mouse anti-serum albumin antibody (Santa Cruz). Antimouse IgG conjugated to the IR Dye™ 700 DX fluorophore and anti-rabbit IgG conjugated to the IR Dye™ fluorophore (Rockland Immunochemical Inc., Gilbertsville, Pa., United States) were used as secondary antibodies. The bound proteins were visualized using the Odyssey imaging system (LI-COR Biosciences, Lincoln, Nebr., United States) and then quantified by densitometry using the Multigauge software (Fuji film, Tokyo, Japan). The measurements are expressed in optical density units (ODU).

In order to evaluate the reliability of the measurements of the levels of total PKR and of pPKR446, the inventors carried out a test-retest study on the CSF of 25 randomly selected individuals, and calculated the intraclass correlation coefficient between two successive measurements of the levels of total PKR and of pPKR446.

Statistical Analyses

The characteristics of the individuals are presented according to their clinical diagnosis (neurological controls or controls (NC), mild cognitive impairment (MCI) and Alzheimer's disease (AD)) and compared between the three groups using the $\chi^2$ test for categorical variables and analysis of variance for continuous variables. The analysis of ROC (Receiving Operating Characteristics) curves was used to determine the discriminating capacity of total PKR, pPKR446 and the pPKR446/total PKR ratio for differentiating between the NC and AD individuals. The optimal cutoff threshold values were identified by maximizing the Youden index (sensitivity+specificity−100). The correlation between the various biomarkers was evaluated using the Pearson correlation coefficients. All the p values were two-sided and a P value of less than or equal to 0.05 was considered to be statistically significant. The statistical analyses were carried out using the SAS software version 9.2 (SAS Institute, Cary, N.C., Unites States) and the Stata software version 10.0 (Statacorp LP, College Station, Tex., United States).

2. Results

Among the 108 individuals included, 6 AD, 10 controls (NC) and 1 MCI were excluded for technical reasons related to the CSF analysis (8 because of an insufficient amount of CSF and 9 because a protein concentration that was too low in the CSF). These individuals did not differ from the individuals included with regards to age and gender ratio. A total of 91 individuals was therefore finally included in the study (AD, n=45; amnestic MCI, n=11; NC, n=35). The NC individuals were directed to the Centre Mémoire [Memory Center] of the Lariboisière hospital for cognitive complaints (major anxiety-depressive disorders 14, stroke complication 5, alcohol dementia 4, sleep apnea syndrome 2, Sjögren's syndrome 2, sarcoidosis 1, multiple sclerosis 2, amyotrophic lateral scleroses 1, Lyme disease 1, normal pressure hydrocephalus 1, epilepsy 1, peripheral neuropathy 1).

The clinical characteristics of the AD, MCI and NC individuals are given in table 4 below:

TABLE 4

Characteristics of the individuals in the study

| | NC (n = 35) | MCI (n = 11) | AD (n = 45) | P |
|---|---|---|---|---|
| Characteristics | | | | |
| Age (years) | 64.0 (9.2) | 76.9 (10.5) | 70.8 (9.1) | <0.001 |
| Women, n (%) | 23 (65.7) | 7 (63.6) | 28 (62.2) | 0.95 |
| MMSE | 25.7 (3.4) | 24.1 (1.7) | 19.6 (6.5) | 0.001 |
| CSF biomarkers (pg/ml) | | | | |
| Aβ42 | 808.8 (183.9) | 608.7 (276.4) | 414.7 (150.6) | <0.001 |
| T-tau | 189.6 (59.2) | 316.1 (124.2) | 590.7 (328.7) | <0.001 |
| ptau181 | 45.1 (12.8) | 63.1 (18.8) | 106.3 (52.5) | <0.001 |
| PKR# in the CSF | | | | |
| Total PKR | 52.2 (9.6) | 75.3 (21.6) | 72.5 (12.6) | <0.001 |
| pPKR446 | 29.0 (13.9) | 85.0 (40.4) | 92.3 (38.0) | <0.001 |
| pPKR446/total PKR | 0.55 (0.23) | 1.10 (0.37) | 1.25 (0.38) | <0.001 |

Except for the number of women, the values indicated represent the mean of the individuals, the standard deviation is indicated between parentheses;
MMSE: score in the Mini Mental Status Examination cognitive test;
optical density units The average age is slightly lower in the NC individuals compared with the AD individuals. The CSF biomarkers Aβ42, T-tau and ptau181 are significantly different in the AD and MCI individuals compared with the NC individuals. The determination of the levels of total PKR and of pPKR446 and of the pPKR446/total PKR ratio is carried out in the same samples of CSF for the three groups of individuals. The level of total PKR, and in particular the level of pPKR446, are elevated in the AD individuals.

Figure 9:
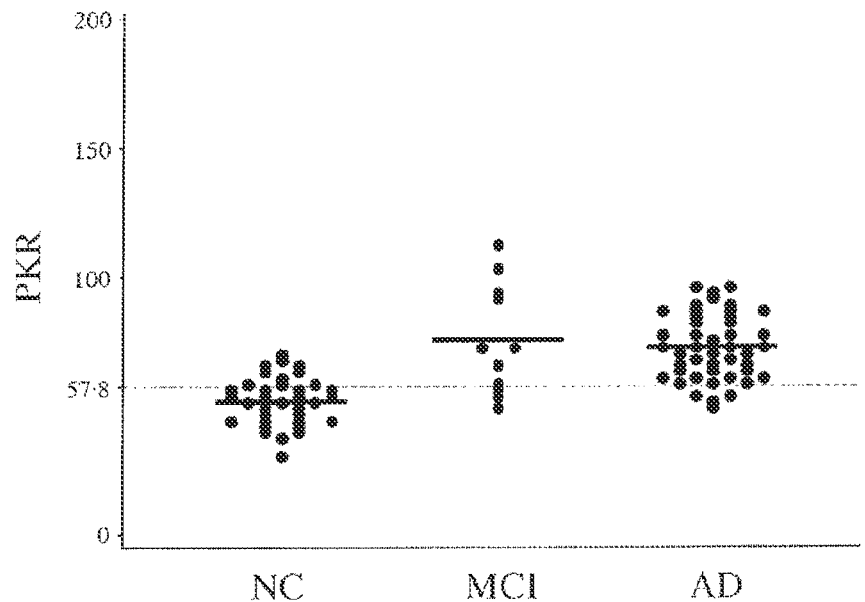
FIGS. 9, 10, 11
Figure 10:
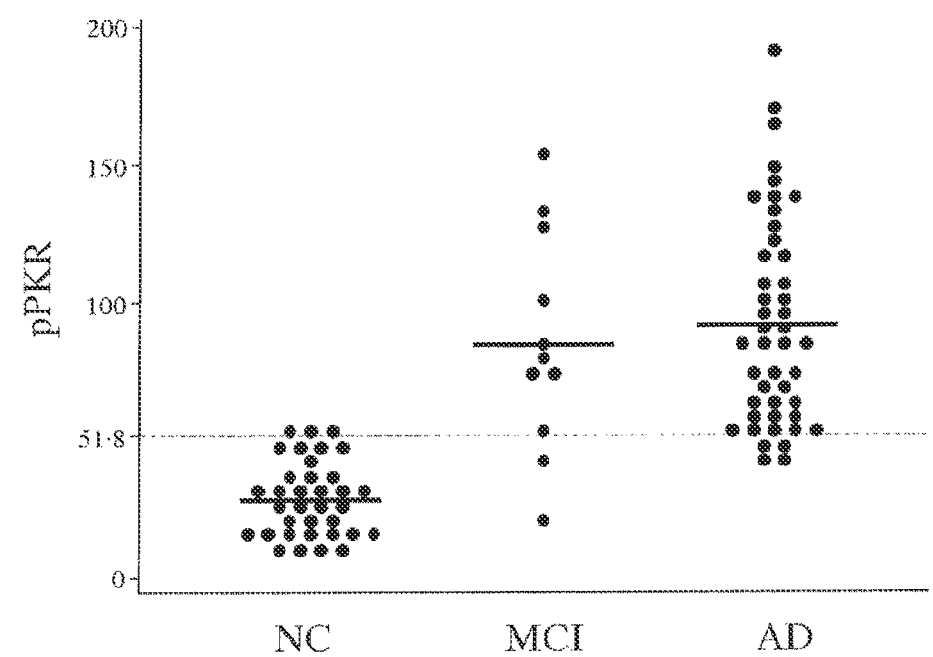
Figure 11:
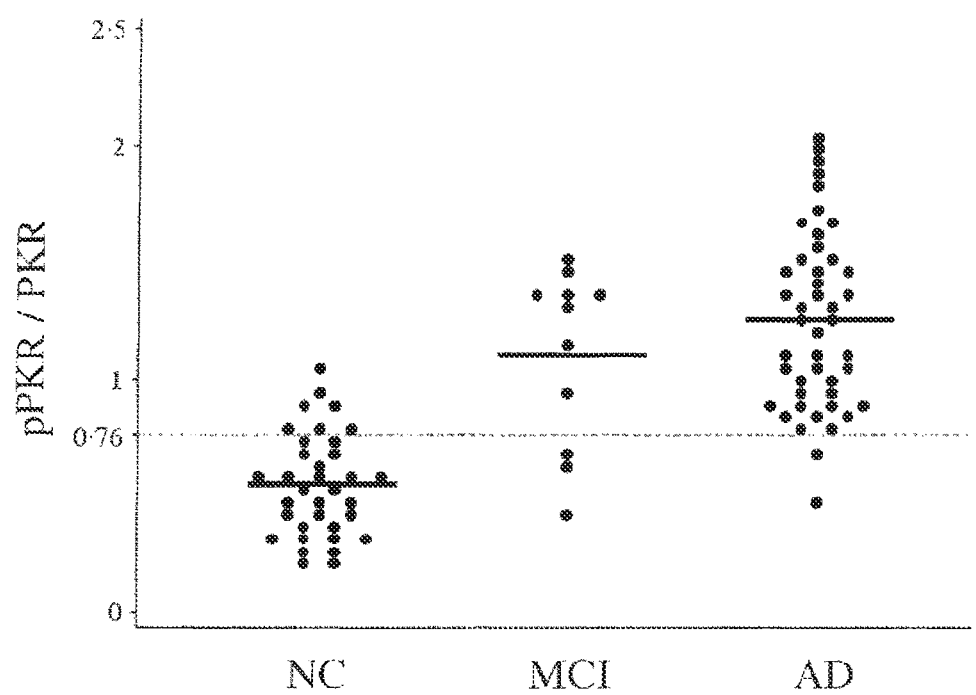

It is in particular observed that there is a statistically significant difference between the three groups as regards the levels of total PKR and of pPKR446, and the pPKR446/total PKR ratio. For example, the mean level of pPKR is 29.0+/−13.9 in the NC individuals, 85.0+/−40.4 in the MCI individuals and 92.3+/−38.0 in the AD individuals (ODD). This is also visible in FIGS. 9-11 which present the results of the individuals and the threshold value determined below.

Table 5 below gives the results of the ROC curves established for the level of total PKR, the level of pPKR446 and the pPKR446/total PKR ratio regarding the discrimination between the AD and NC individuals.

TABLE 5

Area under the curve (AUC) of the ROC curves

| Biomarkers | AUC (SE) | Threshold value | Sensitivity (%) | Specificity (%) | Youden |
|---|---|---|---|---|---|
| Aβ42 | 0.95 (0.02) | 606 | 96.7 | 88.9 | 0.86 |
| T-tau | 0.95 (0.02) | 282 | 91.1 | 96.7 | 0.88 |
| ptau181 | 0.95 (0.02) | 61 | 88.9 | 90.0 | 0.79 |
| Total PKR | 0.90 (0.03) | 57.8 | 91.1 | 71.4 | 0.63 |
| pPKR446 | 0.98 (0.01) | 51.8 | 91.1 | 94.3 | 0.85 |
| pPKR446/total PKR | 0.95 (0.02) | 0.76 | 95.6 | 82.9 | 0.79 |

SE: Standard error

The area under the curve (AUC) is 0.98 for pPKR446 and 0.95 for pPKR446/total PKR. Thus, a threshold value of 51.8 ODU for pPKR446 makes it possible to distinguish AD individuals from NC individuals, with a sensitivity of 91.1% and a specificity of 94.3%. These values are of the same order as those determined for Aβ42, T-tau and ptau181 in the same samples of CSF. It is noted that the AUC value associated with pPKR446 is the best regardless of the marker considered, including the conventional CSF markers Aβ42, T-tau and ptau181.

The test-retest, i.e. the double determination of the levels of the markers in one and the same sample in order to study the reliability of the measurement, was carried out on 25 samples of CSF (10 NC, 2 MCI and 13 AD). Reliable values of the intraclass correlation coefficients between two consecutive measurements of total PKR and of pPKR446 were able to be demonstrated (respectively 0.94 and 0.97).

On the other hand, no correlation was able to be established between the levels of total PKR and pPKR446 and the age or the MMSE scores. Moreover, it is observed that, in the AD individuals, the level of pPKR446 is more elevated in men than in women.

The inventors also studied the correlation between the level of total PKR, the level of pPKR446, the pPKR446/total PKR ratio and the levels of Aβ42, T-tau and ptau181 in the AD and NC individuals (table 6).

TABLE 6

Correlation between the level of total PKR, the level of pPKR446, the pPKR446/total PKR ratio and the levels of Aβ42, T-tau and ptau181

| | Pearson correlation coefficient | | | | | |
|---|---|---|---|---|---|---|
| | Aβ42 | | T-tau | | ptau181 | |
| | r | p | r | p | r | p |
| AD (n = 45) | | | | | | |
| Total PKR | −0.10 | 0.33 | 0.29 | 0.06 | 0.31 | 0.041 |
| pPKR446 | 0.04 | 0.79 | 0.17 | 0.26 | 0.30 | 0.045 |
| pPKR446/total PKR | 0.14 | 0.36 | 0.05 | 0.73 | 0.19 | 0.21 |
| NC (n = 35) | | | | | | |
| Total PKR | −0.12 | 0.51 | 0.17 | 0.36 | 0.20 | 0.40 |
| pPKR446 | −0.02 | 0.90 | 0.27 | 0.15 | 0.04 | 0.83 |
| pPKR446/total PKR | 0.06 | 0.77 | 0.25 | 0.18 | 0.15 | 0.44 |

It is observed that, in the AD individuals, the ptau181 concentrations are correlated with the levels of total PKR and of pPKR446, but with a low correlation coefficient. On the other hand, no correlation is found between the levels of total PKR or of pPKR446 and those of Aβ42 and of T-tau in the AD individuals. Furthermore, no correlation could be demonstrated between the level of total PKR or the level of pPKR446 and the levels of Aβ, T-tau and ptau181 in the NC individuals.

This therefore indicates that the level of total PKR, the level of pPKR446 or the pPKR446 ratio provide information that is essentially independent with respect to the conventional CSF markers, thereby making it possible in particular to anticipate that combining the level of total PKR, the level of pPKR446, or the pPKR446 ratio, with the levels of Aβ42, T-tau and ptau181 would make it possible to improve the effectiveness of the current tests based on these markers.

Moreover, the inventors observed that, in the 45 AD individuals, 6 showed samples of CSF which did not meet the criteria of positivity for the levels of Aβ42, T-tau and ptau181, but which nevertheless showed increased levels of pPKR446 and of the pPKR446/total PKR ratio (table 7).

TABLE 7

Determination of the level of total PKR, of the level of pPKR446, and of the pPKR446/total PKR ratio in AD individuals for whom the levels of Aβ42, T-tau and ptau181 are normal

| | | | | | Biomarkers | | | | | |
|---|---|---|---|---|---|---|---|---|---|---|
| Individuals | Sex | Age | Diagnosis | MMSE | Aβ42 | T-tau | ptau181 | T-PKR | pPKR | pPKR/T-PKR |
| Patient 1 | F | 77.5 | AD | 26 | 647 | 195 | 41 | 49.8 | 73.7 | 1.48 |
| Patient 2 | F | 82.2 | AD | 27 | 802 | 282 | 59 | 57.9 | 55.3 | 0.96 |
| Patient 3 | F | 81.6 | AD | 22 | 865 | 184 | 47 | 53.6 | 63.1 | 1.18 |

TABLE 7-continued

Determination of the level of total PKR, of the level of pPKR446, and of the pPKR446/total PKR ratio in AD individuals for whom the levels of Aβ42, T-tau and ptau181 are normal

| Individuals | Sex | Age | Diagnosis | MMSE | Aβ42 | T-tau | ptau181 | T-PKR | pPKR | pPKR/T-PKR |
|---|---|---|---|---|---|---|---|---|---|---|
| Patient 4 | F | 88.0 | AD | 19 | 641 | 191 | 46 | 85.2 | 92.6 | 1.09 |
| Patient 5 | M | 66.7 | AD | 26 | 279 | 195 | 56 | 84.5 | 141.1 | 1.67 |
| Patient 6 | F | 67.8 | AD | 26 | 751 | 420 | 74 | 68.9 | 135.7 | 1.97 |

T-PKR = total PKR;
pPKR = pPKR446

Thus, the evaluation of total PKR and of pPKR446 can demonstrate an anomaly, although the conventional biomarkers do not show it, which reinforces their advantage and confirms that the biomarkers of the invention provide information that is essentially independent of that of the conventional biomarkers.

Finally, the inventors compared the levels of the various biomarkers in the MCI individuals (table 8).

TABLE 8

Determination of the level of total PKR, of the level of pPKR446 and of the pPKR446/total PKR ratio in amnestic MCI individuals

| Individuals | Sex | Age | MCI | MMSE | Aβ42 | T-tau | p181tau | T-PKR | pPKR | pPKR/T-PKR |
|---|---|---|---|---|---|---|---|---|---|---|
| Patient 1 | F | 76.7 | stable | 26 | 924 | 399 | 85 | 90.9 | 131.6 | 1.45 |
| Patient 2 | F | 82.1 | Converted | 22 | 664 | 206 | 35 | 55.9 | 72.4 | 1.29 |
| Patient 3 | F | 85.3 | Stable | 24 | 312 | 288 | 59 | 113.2 | 72.6 | 0.64 |
| Patient 4 | M | 82.4 | Converted | 26 | 870 | 328 | 79.5 | 64.5 | 43.5 | 0.67 |
| Patient 5 | F | 79.5 | Converted | 26 | 447 | 270 | 44 | 102.5 | 154.9 | 1.51 |
| Patient 6 | F | 86.5 | Stable | 24 | 265 | 602 | 89 | 94.0 | 126.6 | 1.34 |
| Patient 7 | F | 66.9 | stable | 24 | 854 | 253 | 64 | 53.3 | 51.4 | 0.97 |
| Patient 8 | M | 49.9 | stable | 23 | 309 | 109 | 36 | 49.9 | 20.5 | 0.41 |
| Patient 9 | F | 79.6 | stable | 27 | 332 | 357 | 58 | 72.4 | 98.8 | 1.36 |
| Patient 10 | M | 74.5 | Converted | 22 | 795 | 358 | 74 | 59.4 | 79.6 | 1.34 |
| Patient 11 | M | 83.2 | Converted | 23 | 924 | 307 | 71 | 72.2 | 82.8 | 1.15 |

T-PKR = total PKR;
pPKR = pPKR446;
Stable indicates no change to Alzheimer's disease over the duration of the study;
Converted indicates a change to Alzheimer's disease over the duration of the study It is observed that, for a cutoff value of 51.8 ODU regarding the level of pPKR446, 81.8% of the amnestic MCI individuals exhibited an abnormal level of pPKR446. Among the five individuals who developed Alzheimer's disease over the duration of the study, which lasted 1 year, just one of the individuals exhibited normal levels of total PKR and of pPKR446. In comparison, just one of the five individuals exhibited an abnormal level of Aβ42 and only three of the five individuals exhibited an abnormal level of T-tau and of ptau181. It therefore appears that the biomarkers of the invention could be more sensitive than Aβ42, T-tau and ptau181 for identifying, among MCI individuals, those who are at an early, asymptomatic stage of Alzheimer's disease, or those who are at risk of developing Alzheimer's disease in the short term.

Moreover, among the six stable MCI patients, four exhibited abnormal levels of total PKR and of pPKR446. A study over a longer period of time will make it possible to evaluate whether these individuals actually develop Alzheimer's disease.

The invention claimed is:

1. A method of detecting an elevated level of phosphorylated double-stranded RNA-dependent protein kinase (PKR) in an individual suspected of having a neurodegenerative disease, comprising the steps of:
   (i) obtaining a sample of cerebrospinal fluid isolated from the individual,
   (ii) measuring the level of phosphorylated PKR in the sample using an immunoassay comprising contacting the sample of cerebrospinal fluid with a monoclonal antibody, an antibody fragment or an aptamer specifically recognizing said phosphorylated PKR, and
   (iii) measuring the level of total PKR in the sample using an immunoassay comprising contacting the sample of cerebrospinal fluid with a monoclonal antibody, an antibody fragment or an aptamer specifically recognizing said PKR,
   wherein an individual with elevated PKR has a-ratio of the level of phosphorylated PKR obtained in step (ii) to the level of total PKR obtained in step (iii) of about 2-fold greater than the ratio of the level of phosphorylated PKR to the level of total PKR in a normal individual.

2. The method as claimed in claim 1, wherein the neurodegenerative disease is selected from the group consisting of Alzheimer's disease, Huntington's disease, Creutzfeldt-Jakob disease and Parkinson's disease.

3. The method of claim 1, wherein the neurodegenerative disease is Alzheimer's disease.

4. The method of claim 1, wherein the individual is not suffering from dementia.

5. The method of claim 1, wherein the individual is suffering from mild cognitive impairment (MCI).

6. The method as claimed in claim 1, wherein said method further comprises measuring in said sample of cerebrospinal fluid, the level of at least one biological marker of neurodegenerative disease selected from the group consisting of the marker β-amyloid (Aβ), total tau (T-tau) and phosphorylated tau (ptau), wherein the level of said at least one biological marker of neurodegenerative disease is normal.

* * * * *